United States Patent
Le Bras et al.

[11] Patent Number: 5,858,381
[45] Date of Patent: *Jan. 12, 1999

[54] COSMETIC COMPOSITION INTENDED FOR MAKING UP THE SKIN, PROCESS FOR ITS PREPARATION AND MAKE-UP PRODUCT OBTAINED FROM SAID COMPOSITION

[75] Inventors: Véronique Le Bras, Paris; Philippe Gabin, Bures sur Yvette, both of France

[73] Assignee: L'Oreal, Paris, France

[*] Notice: The term of this patent shall not extend beyond the expiration date of Pat. No. 5,223,559.

[21] Appl. No.: 846,469

[22] Filed: May 1, 1997

Related U.S. Application Data

[63] Continuation of Ser. No. 337,821, Nov. 8, 1994, abandoned.

[30] Foreign Application Priority Data

Nov. 8, 1993 [FR] France .................................. 93 13238

[51] Int. Cl.$^6$ ................ A61K 7/06; A61K 7/48
[52] U.S. Cl. ................... 424/401; 424/69; 424/63; 424/64; 514/937
[58] Field of Search .............. 424/401, 69, 63, 424/64; 514/937

[56] References Cited

U.S. PATENT DOCUMENTS

| | | |
|---|---|---|
| 4,994,264 | 2/1991 | Verdon et al. . |
| 5,219,561 | 6/1993 | Gagnebien et al. . |
| 5,223,559 | 6/1993 | Arraudeau et al. . |

FOREIGN PATENT DOCUMENTS

| | | |
|---|---|---|
| 0447286 | 9/1991 | European Pat. Off. . |
| 0502769 | 9/1992 | European Pat. Off. . |
| 2540877 | 9/1976 | Germany . |
| 1519373 | 7/1978 | United Kingdom . |

OTHER PUBLICATIONS

Database WPI Week 8006, Derwent Publications Ltd., AN80–10351C & JP–A–54 163 831 (no other date available).

Database WPI Section Ch, Week 8622, Derwent Publication Ltd., Class D08, AN 86–141933 & JP–A–61 078 709 (no other date available).

Database WPI Section Ch, Week 9139, Derwent Publications Ltd., Class D08, AN 91–296066 & JP–A–3 190 813 (no other date).

Patent Abstracts of Japan, vol. 15, No. 445 (C–0884) Nov. 1991 & JP–A–03 190 813 (no other date).

*Primary Examiner*—Sally Gardner-Lane
*Attorney, Agent, or Firm*—Nixon & Vanderhye, P.C.

[57] ABSTRACT

This composition includes a pulverulent fraction of relative density D, compatible with application to the skin, dispersed in a binder consisting of an emulsion comprising a fatty phase and an aqueous phase, in which:

the particles of the said fraction have dimensions of between 0.5 and 100 $\mu$m, the particle concentration per unit volume of said composition is at least equal to the critical particle concentration C*, and the filler content F, defined in % by the formula:

$$F = 100 \times \frac{\text{weight of the pulverulent fraction excluding pigments}}{\text{total weight of the composition}}$$

is between F0 and 1.8×F0, the value F0 being calculated as follows:

if $D \leq 0.1$ F0=10 if $0.1 < D \leq 0.6$ F0=(60×D)+4 if D>0.6 F0=40. The invention also relates to the corresponding process of preparation and the make-up product obtained.

21 Claims, 1 Drawing Sheet

COSMETIC COMPOSITION INTENDED FOR MAKING UP THE SKIN, PROCESS FOR ITS PREPARATION AND MAKE-UP PRODUCT OBTAINED FROM SAID COMPOSITION

This is a continuation of application Ser. No. 08/337,821, filed Nov. 8, 1994, now abandoned.

BACKGROUND OF THE INVENTION

The present invention relates to a cosmetic composition with a high filler content, intended for making up the skin. The invention also relates to a process for preparing said composition by extrusion in a screw mixer. Finally, the invention relates to a make-up product making use of the said composition.

PRIOR ART

It is known that cosmetic compositions containing a powder dispersion are very widely employed for blurring skin defects such as microreliefs and wrinkles and for blurring color variations or for imparting a desired color to the skin. Make-up products of this type are generally presented in the form of liquid or creamy foundation or in the form of compacted tablet. In all cases the compositions used consist of powders dispersed in a binder. The powders generally contain colored pigments such as iron oxides, and particulate fillers, such as mica, talc or silica. A composition has been described, for example, in U.S. Pat. No. 4,839,163, in which the binder is an oil-in-water emulsion in which a pulverulent fraction is dispersed containing essentially lamellar fillers which impart a good hiding power to the composition; unfortunately, these lamellar fillers function above all by reflecting the light and, for this reason, have the disadvantage of giving the skin a not very natural shiny appearance.

Attempts have therefore been made, while preserving the hiding power, that is to say a good ability to mask the skin imperfections, to improve the translucency of the make-up obtained with such compositions, to give the made-up skin a natural appearance. To do this, it has been proposed, for example in Japanese Patent Application 61-69,708, to prepare compositions in which the filler particles are coated with an acrylic resin; the disadvantage is that the preparation of such a composition requires a preliminary filler coating treatment, a coating whose integrity in the final formulation is furthermore not ensured.

In French Patent 2,673,372 a composition has also been proposed which makes it possible to produce a translucent make-up layer blurring the reliefs of the skin properly and neverthless giving the made-up skin a natural appearance; this result is achieved by dispersing a powder whose particles are spherical or spheroidal in an oily binder, besides the lamellar pigments and powders, and by conforming to a determined binder/powder(s) volume ratio. More precisely, this composition comprises, dispersed in a binder made up of an emulsion comprising an oily phase and an aqueous phase, a pulverulent fraction consisting of at least one powder and compatible with the application to the skin, the particle concentration per unit volume C of the said composition being defined by the formula:

$$C = \frac{V_{CT}}{V_{CT} + V_G}$$

where $V_{CT}$ denotes the volume of the total pulverulent fraction and $V_G$ denotes the volume of the nonvolatile oils in the oily phase of the binder, a volume which is obtained by subtracting from the total volume of the fatty phase, including any oil-soluble ingredients, that, if any, corresponding to the oils which at 25° C. have a saturated vapor pressure higher than 50 Pa, the critical value C* of the concentration C defined above being that at which $V_G$ is equal to the volume just necessary to fill the interstices between the particles of the pulverulent fraction, as measured according to ASTM standard D 281–84, C being at least equal to C*. In this composition the pulverulent fraction contains at least 75% by weight of spherical or spheroidal particles and C* is between 3 and 90%. However, as emerges from the examples of this patent, the quantity of filler incorporated in this type of composition is limited in practice because, starting with a certain percentage, the composition becomes too pasty to permit a correct homogenization by means of the turbine mixers conventionally employed for producing these emulsions; the appearance of the emulsion becomes grainy and matt, which is the sign of a heterogeneous composition. Now, it is extremely advantageous to increase the percentage of filler(s) in a make-up composition of this type, to improve the hiding power and the blurring of the skin reliefs.

In Japanese Patent Application 54/163,831, published on Dec. 26, 1979, an anhydrous make-up composition has been proposed containing, dispersed in a fatty binder, a high proportion of a pulverulent fraction consisting of a mixture of pigments and of mica powder. The manufacture of this composition is performed by producing a mixture, with water or volatile solvents, containing the various constituents of the composition, by extruding the mixture obtained and by drying the extruded product. Unfortunately, the fillers in the makeup product thus produced, apart from the pigments which give the color, consist exclusively of mica powder, that is to say a lamellar powder which, as already indicated earlier, gives the make-up a not very natural reflecting appearance which it is desirable to avoid.

DESCRIPTION OF THE INVENTION

It has now been discovered, according to the present invention, that it is possible to introduce a high percentage of fillers into an emulsion on condition of conforming to a rule defining the filler content as a function of the density of the pulverulent faction employed. In the case of formulations which make it possible to blur wrinkles it is known, especially from the abovementioned French Patent 2,673, 372, that the blurring capacity is related to the fact that the particle concentration per unit volume C, defined above, is higher than the critical particle concentration per unit volume C*, also defined above; the higher the C/C* ratio, the higher the blurring capacity of the composition; however, hitherto it was considered that the reduction in the proportion of fatty phase, which corresponds to an increase in the value of C at constant fillings, entailed a reduction in the comfort on the skin and an increase in the tendency of the emulsion to instability; moreover, as has already been indicated above, the increase in the filler volume at constant quantity of fatty phase, which also corresponds to an increase in the value of C, had a ceiling due to the heterogeneity of the final composition. According to the invention it has now been found that, if the choice of the filler content F, defined later, is kept in a specific range, it is possible to obtain by extrusion a perfectly homogeneous pasty composition which, when employed for making up the skin, is found to have a remarkable hiding power and which allows a translucent make-up of completely natural appearance to be obtained. In addition, the compositions according to the invention, although having a high filler content, contain sufficient volumes of oil for the paste obtained to be malleable and easy to form. This composition can therefore be packaged in the form of a rod (or stick) which is stored in a leakproof packaging and which, on application to the skin, gives the pleasant impression of a powder with a feeling of coolness; such a composition can also be packaged in particulate form, for example as beads, vermicelli or granules, by adding a granulator at the extruder exit, these particles being suspended in a gel for the application. It must be noted that the inclusion of the particles in a gel is facilitated because of the hydrophilicity of the composition, which is an emulsion. When applied, the gel allows the particles to spread and the user has an impression of melting and a sensation of cooling; after drying on the skin a thin powder film remains which has a high wrinkle-blurring power.

The compositions according to the invention may also contain so-called "noncompactable" fillers. "Noncompactable fillers" are intended to mean a raw material which, starting with a certain percentage in a mixture of powders, does not make it possible to carry out a compacting by means of a mechanical press or results in unsatisfactory compacting; actually it is known that, in cosmetics, a compacted tablet must meet a certain number of criteria, especially maintaining the integrity of the compact in time, obtaining a planar surface for the compact and the toughness of the compact in the event of impact. Microspheres, microcapsules and lamellar powders can be found among the so-called "noncompactable" materials. To give an example, it may be indicated that if hollow microspheres made of a thermoplastic material with a relative density of less than 0.1 are employed as filler in a compacted make-up product, the appearance of initiation of cracking and of break-up is found as soon as the percentage of these microspheres in the composition is higher than approximately 1% by weight, this deterioration being the result of relaxation phenomena. The pasty composition obtained according to the invention can, surprisingly, be compacted by conventional means such as a mechanical press, even in the event of the presence of a high proportion of so-called "noncompactable" raw materials, because the presence of water ensures the cohesion; the compacted paste can then be dried, at ambient temperature or in the oven, to obtain a dry powder tablet which has the property of containing fillers considered to be "noncompactable". The pasty composition according to the invention can also be formed in any manner whatever, especially by molding, and then dried by conventional methods. As a result it is therefore possible to obtain sticks or units of any shape whatever, whereas previously the dry powders had a shape imposed by the compacting receptacles employed. It is appropriate to note that the "noncompactable" fillers include especially the low-density microspheres which provide a very soft feel and whose introduction into the compacted powders was hitherto restricted to very small quantities, which is no longer the case with the compositions according to the invention.

DESCRIPTION OF THE PREFERRED EMBODIMENTS

The subject matter of the present invention is consequently a cosmetic composition intended for making up the skin, including a pulverulent fraction of relative density D, compatible with application to the skin, dispersed in a binder consisting of an emulsion comprising a fatty phase and an aqueous phase, in which:

the particles of said fraction have dimensions of between 0.5 and 100 μm, the particle concentration per unit volume of said composition is at least equal to the critical particle concentration and the filler content F, defined in % by the formula:

$$F = 100 \times \frac{\text{weight of the pulverulent fraction excluding pigments}}{\text{total weight of the composition}}$$

is between F0 and 1.8×F0, the value F0 being calculated as follows:

if $D \leq 0.1$ F0=10 if $0.1 < D \leq 0.6$ F0 =(60×D)+4 if $D > 0.6$ F0=40

In the present description the particle concentration per unit volume C of the composition is defined by the formula $C = V_{CT}/(V_{CT}+V_G)$ where $V_{CT}$ denotes the volume of the whole pulverulent fraction and $V_G$ denotes the volume of the nonvolatile constituents of the fatty phase of the binder, a volume which is obtained by subtracting from the total volume of the fatty phase, including any oil-soluble ingredients, that, if any, corresponding to the oils which at 25° C. have a saturated vapor pressure higher than 50 Pa.

The critical value C* of the concentration C defined above is that at which $V_G$ is equal to the volume just needed to fill the interstices between the particles of the pulverulent fraction as measured according to ASTM standard D 281–84.

The pulverulent fraction may include any known powders usually employed for the preparation of cosmetic make-up compositions; these powders may comprise at least one pigment and/or at least one filler. A pulverulent fraction is preferably chosen for which 10%<C*<80%; moreover, C>80% is advantageously chosen.

In addition, if D>0.6 a powder content F of between 40% and 65% is advantageously chosen.

The pigments may be chosen from inorganic pigments, organic pigments and pearlescent pigments.

Among the inorganic pigments there may be mentioned, by way of examples:

titanium dioxide (rutile or anatase), optionally surface-treated and codified in the "Colour Index" (CI) under reference C.I. 77891;

black, yellow, red and brown Iron Oxides (C.I. 77499, 77492, 77491);

Manganese Violet (C.I. 77742);

Ultramarine Blue (C.I. 77007);

Chromium Oxide (C.I. 77288);

Chromium Oxide hydrate (C.I. 77289) and

Ferric Blue (C.I. 77510).

The following pigments may be mentioned, for example, among organic pigments: D & C Red No. 19 (C.I. 45170); D & C Red No. 9 (C.I. 15585); D & C Red No. 21 (C.I. 45380); D & C Orange No. 4 (C.I. 15510); D & C Orange No. 5 (C.I. 45370); D & C Red No. 27 (C.I. 45410); D & C Red No. 13 (C.I. 15630); D & C Red No. 7 (C.I. 15850:1); D & C Red No. 6 (C.I. 15850:2); D & C Yellow No. 5 (C.I. 19140); D & C Red No. 36 (C.I. 12085); D & C Orange No. 10 (C.I. 45425); D & C Yellow No. 6 (C.I. 15985); D & C Red No. 30 (C.I. 73360); D & C Red No. 3 (C.I. 45430); Carbon Black (C.I. 77266) and the lakes based on Cochineal Carmine (C.I. 75470).

The pearlescent pigments may be chosen especially from:

white pearlescent pigments such as mica coated with titanium oxide or bismuth oxychloride; and colored pearlescent pigments such as titanium mica with iron oxides, titanium mica with ferric blue or chromium oxide, titanium mica with an organic pigment of the abovementioned type, and pigments based on bismuth oxychloride.

These pigments may represent up to 30% by weight relative to the total weight of the composition.

The fillers are chosen especially from:

talc, which is a hydrated magnesium silicate employed in the form of particles generally smaller than 40 μm in size; talc has moisture-absorbing properties and is employed above all because of its smooth feel;

micas, which are aluminosilicates of various compositions, which are in the form of flakes from 2 to 200 μm, preferably from 5 to 70 μm in size and with a thickness of 0.1 to 5 μm, preferably from 0.2 to 3 μm; the micas may be of natural origin (for example muscovite, margarite, roscoelite, lipidolite, biotite) or of synthetic origin; the micas are generally transparent and enable a satiny look to be imparted to the skin;

starch, in particular rice starch;

kaolin, which is a hydrated aluminum silicate, which is in the form of lamellar particles generally smaller than 30 μm in size and which has good absorption properties for fatty substances;

zinc and titanium oxides, generally employed in the form of particles whose size does not exceed a few micrometers (or even smaller than 1 μm in the case of titanium oxide); these oxides have a smooth feel, have a good hiding power and a high opacity;

precipitated calcium carbonate which, in the form of particles smaller than 10 μm in size, has a smooth feel and enables a matt look to be obtained;

magnesium carbonate and hydrocarbonate, which have especially perfume-fixing properties;

silica;

metal soaps derived from carboxylic organic acids containing from 8 to 22 carbon atoms, preferably from 12 to 18 carbon atoms, for example zinc, magnesium or lithium stearate, zinc laurate or magnesium myristate; these soaps, generally present in the form of particles smaller than 10 μm in size, have a smooth feel and promote the adhesiveness of the powder to the skin.

It is also possible to employ unexpanded synthetic polymer powders such as polyethylene, polyesters (for example polyethylene isophthalate or terephthalate) and polyamides (for example nylon) in the form of particles smaller than 50 μm in size, which have absorbent properties and enable a velvety look to be imparted to the skin; mineral powders such as spherical silica; spherical titanium dioxides like that marketed under the trade name "Spherititan"; glass and ceramic beads marketed by the "3M" company under the trade names "Macrolites"; powdered organic materials of natural origins such as corn, wheat and rice starches, cross-linked or otherwise; synthetic polymer powders, cross-linked or otherwise, spheronized, like polyamide powders such as poly-β-alanine powders and nylon powders like those marketed by the company "Atochem" under the trade name "Orgasol", polyacrylic or polymethacrylic acid powders, polystyrene powders crosslinked with divinylbenzene, silicone resin powders, teflon powders like those marketed by the "Montefluos" company under the trade name "Fluon" or those marketed by the "Hoechst" company under the trade name "Hostaflong".

As follows from the above listing, the pulverulent fraction may include at least one so-called "noncompactable" filler, and this is an important characteristic of the invention because, if the composition according to the invention is molded or compacted and if it is subsequently dried, an anhydrous make-up product is obtained which has the desired form and contains a high proportion of "noncompactable" fillers which was completely impossible in the state of the art. Under the heading "noncompactable fillers" there are included especially:

a) solid microspheres made of any organic or inorganic material compatible with use on the skin, that is to say nonirritant and nontoxic. These microspheres may be microporous, in which case they have a specific surface of at least 0.5 m$^2$/g and of preferably at least 1 m$^2$/g, said specific surface having no upper limit other than that resulting from the practical possibility of producing microspheres of very high porosity; the specific surface may, for example, reach 1,000 m$^2$/g or even more. By way of examples there may be mentioned the microporous microspheres sold by the "Dow Corning" company under the trade name "Polytrap" and the microporous microspheres from the "Seppic" company sold under the trade name of "Micropearl M" or "Micropearl M 100". The microporous microspheres may be unimpregnated or impregnated, especially with active agents; the "Plastic Powder FBSQ" microspheres impregnated with squalane and the "Silica Beads" microspheres may be mentioned in this respect;

b) hollow microspheres made of thermoplastic material and prepared by known processes, such as those described in U.S. Pat. No. 3,615,972 and EP-A-056,219. These hollow microspheres may especially be made of polymers or copolymers of ethylene derivatives, such as polyethylene, polystyrene, vinyl chloride/ acrylonitrile copolymer, or polyacrylonitrile, of polyamides, of polyesters, of urea-formaldehyde polymers or of vinylidene chloride copolymers such as the vinylidene chloride/acrylonitrile copolymer. It is possible to mention, for example, the hollow microspheres marketed under the trade name "Expancel" by the "Kemanord Plast" company or under the trade name "Micropearl F 80 ED" by the "Matsumoto" company;

c) microcapsules made of any organic or inorganic material compatible with use on the skin, that is to say nonirritant and nontoxic. These microcapsules may or may not contain an active agent. Microcapsules made of polymeric organic material are made, especially, of polymers or copolymers derived from acids, amines or monomer esters containing ethylenic unsaturation, of ureaformaldehyde polymers, or of vinylidene chloride polymers or copolymers. By way of illustrations there will be mentioned microcapsules made of methyl acrylate or methacrylate polymers or copolymers or vinylidene chloride/ acrylonitrile copolymers; among the latter, those containing, by weight, from 20 to 60% of units derived from vinylidene chloride, from 20 to 60% by weight of units derived from acrylonitrile and from 0 to 40% by weight of other units such as units derived from an acrylic or styrene-based monomer will be indicated in particular.

By way of examples there may be mentioned the "Macrolite" microcapsules sold by the "3M" company, the "Q-Max" microcapsules sold by the "Q-Max" company and the "3M" microcapsules sold by the "3M" company;

d) certain lamellar fillers and especially titaniummicas, certain sericites, such as that sold by the "Whittaker" company under the trade name "Sericite BC 282" and certain talcs, such as that sold by the "Nippon" company under the trade name "Talc K 1" or that sold by the "Luzenac" company under the trade name "Extra Steamic OOS".

It is appropriate, moreover, to indicate that the pigments and the fillers may be coated with substances such as amino acids, silicones, metal salts or collagen, especially to modify their surface state.

In an advantageous embodiment, the emulsion which constitutes the binder of the composition according to the invention includes a large quantity of water; it is preferred for the composition to contain from 25 to 50% by weight of water and, better, from 30 to 45% by weight of water. The fatty phase of the emulsion includes at least one fatty constituent which is liquid or solid at ambient temperature.

Among the fatty constituents that can be employed, there may be mentioned, especially, fatty substances or oils of animal, vegetable, mineral or synthetic origin, waxes of animal, vegetable, mineral or synthetic origin, or mixtures thereof.

The fatty substances or oils are chosen in particular from mink oil, turtle oil, soya oil, grapeseed oil, sesame oil, corn oil, rape oil, sunflower oil, cottonseed oil, avocado oil, olive oil, castor oil, jojoba oil or peanut oil, a hydrocarbon oil such as paraffin oils, squalane and vaseline, esters such as isopropyl myristate, isopropyl palmitate, butyl stearate, hexyl laurate, isononyl isononate, 2-ethylhexyl palmitate, 2-hexyldecyl laurate, 2-octyldecyl palmitate, 2-octyldodecyl myristate, di-2-ethylhexyl succinate, diisostearyl malate, 2-octyldodecyl lactate, glycerine triisostearate or diglycerine triisostearate, a silicone oil such as polymethylsiloxanes, polymethylphenylsiloxanes, polysiloxanes modified with fatty acids, polysiloxanes modified with fatty alcohols, polysiloxanes modified with polyoxyalkylenes, fluorinated silicones, perfluorinated and/or organofluorinated oils, higher fatty acids such as myristic acid, palmitic acid, stearic acid, behenic acid, oleic acid, linoleic acid, linolenic acid or isostearic acid, and higher fatty alcohols such as cetanol, stearyl alcohol or oleyl alcohol.

The waxes may be chosen from the group made up of animal waxes, vegetable waxes, mineral waxes, synthetic waxes and the various fractions of natural waxes. Among the animal waxes which can be employed there may be mentioned beeswaxes, lanolin waxes and China insect waxes. Among the vegetable waxes there may be mentioned carnauba, candelilla and ouricury wax, cork fiber waxes, sugar cane waxes, Japan waxes, hydrogenated jojoba waxes and the hydrogenated oils which are obtained by catalytic hydrogenation of fatty substances composed of $C_8$–$C_{32}$ linear or nonlinear fatty chains and which have the properties corresponding to the definition of waxes. In particular, there may be mentioned hydrogenated sunflower oil, hydrogenated castor oil, hydrogenated copra oil and hydrogenated lanolin. Among the mineral waxes there may be mentioned paraffins, microcrystalline waxes, montan waxes and ozokerites. Among the synthetic waxes there may be mentioned polyethylene waxes, the waxes obtained by the Fischer and Tropsch synthesis, waxy copolymers and their esters and silicone waxes such as polyalkoxy- and polyalkylsiloxanes.

The fatty phase may, in a known manner, contain at least one lipophilic cosmetic agent and various oil-soluble ingredients generally employed in cosmetics such as, for example, perfumes, it being possible for all these additives to the fatty phase to represent up to 20% by weight relative to the total weight of the fatty phase.

The fatty phase may include volatile oils which at 25° C. have a saturated vapor pressure higher than 50 pascals. When present, these oils generally represent less than 10% by weight relative to the total weight of the composition and less than 20% by weight relative to the weight of the fatty phase. The volatile oils evaporate in contact with the skin when the composition according to the invention is applied to the latter, but are useful because they make it easier for the composition to spread when applied to the skin. Among the volatile oils there may be mentioned, for example, silicone oils such as hexamethyldisiloxane, cyclopentadimethylsiloxane, cyclotetramethylsiloxane, fluorinated oils such as those sold by the "Montefluos" company under the trade name "Galden" and isoparaffinic oils such as those sold under the trade name "Isopar" by the "Esso" company.

The aqueous phase of the emulsion, which constitutes the binder of the composition according to the invention may, in addition to water, contain:

thickeners, such as natural resins, for example gum arabic, tragacanth gum, guar gum, cellulose derivatives, pectins, such as the alginic acid and carrageen derivatives, bentonites and colloidal silicas, polysaccharides, synthetic macromolecules, especially containing vinyl or acrylic groups, starchy materials, phosphorylated derivates of hydroxylated aliphatic alcohol, or interesterified natural or semisynthetic triglycerides;

moisturizers or hydrating agents such as glycerin and collagen;

water-soluble raw materials generally employed in cosmetics.

These additives to the aqueous phase may represent up to 40% by weight relative to the total weight of the composition.

As already indicated, the compositions according to the invention are manufactured by extrusion in a screw mixer. Another subject of the present invention is therefore also a process for preparing a composition as defined above, in which the mixing of the various constituents of said composition is performed in a cooker-extruder mixer comprising, in an outer casing provided with an extrusion die at the exit, one (or two) shaft(s) driven in rotation so that the peripheral structure of a shaft interacts with the outer casing and, where appropriate, with the peripheral structure of the other shaft to ensure blending of the material and its movement in the outer casing towards the extrusion die.

In a preferred embodiment the shaft (or the shafts) consists (consist) of at least two successive sleeves whose inner part is fitted onto an axle driven in rotation and the outer part has a peripheral structure which differs according to the sleeves; the shaft (or each shaft) comprises at least one sleeve forming a conveying screw situated on the feed side of the mixer, at least one sleeve with reverse flight and/or a multilobar sleeve, and at least one sleeve forming a conveying screw situated at the exit end of the mixer. Provision may be advantageously made for the fatty phase of the binder, the aqueous phase of the binder and the pulverulent fraction to be introduced into the mixer simultaneously but at points offset along the shaft(s), with the temperature decreasing from the head of the shaft to the extrusion die; the temperature may be approximately 70°–90° C. in the vicinity of the head of the shaft and may decrease to approximately 20°–30° C. in the vicinity of the extrusion die. The constituents of the fatty phase which are not heat-sensitive or volatile are preferably introduced in the vicinity of the head of the shaft, as is all or part of the pulverulent fraction, the constituents of the aqueous phase which are not heat-sensitive are introduced at a point further away from the head of the shaft and the heat-sensitive or volatile constituents of the emulsion, together with any remainder of the pulverulent fraction are introduced at a point which is still further away from the head of the shaft.

The cooker-extruder mixers that can be employed according to the invention are equipment of known type, commonly used especially in the food industry and the chemical industry. These mixers comprise an outer casing provided with an extrusion die at the exit, a casing inside which one (or two) shaft(s) is (are) driven in rotation so that the peripheral structure of a shaft interacts with the outer casing and, if appropriate, with the peripheral structure of the other shaft, to ensure blending of the material and its travel in the outer casing towards the extrusion die. The shaft (or each of the shafts) preferably consists of at least two successive sleeves, the inner part of which is fitted onto an axle driven in rotation and the outer part of which may have various peripheral structures; among the conventional structures there may be mentioned, on the one hand, a helical screw flight whose pitch drives the material being processed from the entry towards the exit of the mixer (denoted by "NDF" below), on the other hand, a helical screw flight with opposite pitch to the preceding one (denoted by "CF" later, with a negative pitch value), which pushes the material being processed back in the direction running from the exit towards the entry of the mixer, such a flight comprising lengthwise grooves to provide the passage for the material towards the exit of the mixer and, finally, a multilobar section comprising over its whole length small paddles (or lobes) arranged side by side and offset angularly in relation to one another. A bilobar section therefore comprises a succession of lobes offset by 90° in relation to one another and is denoted by "IBL" hereinafter. A sufficiently large number of sleeves with external flights may be arranged to vary the pitch, the depth and the number of flights in the various successive lengthwise zones of the mixer. In addition, the various lengthwise zones of the mixer may be heated by one or more muffs arranged outside the outer casing. The heating may be performed in each muff with the aid of at least one electrical resistance or at least heat exchanger.

According to the invention the shaft (or each shaft) of the cooker-extruder mixer preferably comprises at least one "DF" sleeve forming a conveying screw situated on the feed (or entry) side of the mixer, at least one "CF" (so-called counterflight) sleeve and/or a multilobar "BL" sleeve forming a zone for blending under pressure, and at least one "DF" sleeve forming a conveying screw situated at the exit end of the mixer. The equipment may also comprise at least one sleeve which has a grinding and/or homogenizing action, such as a "BL" bilobar sleeve.

The process according to the present invention has the advantage of being flexible, because the materials introduced as feed, and the feed rates and, consequently, the formulations, can be easily varied. It is also easily possible to vary, as a function of the desired make-up composition, the physical treatment parameters such as the pressure, especially by changing the exit cross-section, the speed of rotation of the shafts, the shearing during processing, especially through the choice of multilobar sleeves and flight shapes, the blending, especially through the choice of sleeves of "CF" type, and the temperature by controlling the muff heaters in line with the various zones of the mixer.

The present invention also relates to a make-up product consisting of the composition according to the invention as extruded by making use of the process described above. The invention also relates to a make-up product consisting of the composition according to the invention which, after extrusion according to the process defined above, has undergone a mechanical molding or compacting operation, optionally followed by drying in air or in an oven.

Finally, the invention relates to a make-up product consisting of a gel containing, dispersed in the particulate state, an extrudate obtained by making use of the process defined above, said extrudate having undergone a granulation to form the particles introduced into said gel.

The examples given below, by way of illustration and without any limitation being implied, will enable the invention to be better understood.

EXAMPLE 1 a) Extruder mixer employed

The operation is carried out in a cooker-extruder mixer with two screws (BC 21 from the "Clextral" company), the structure of which is that outlined below:

| Entry -> | | | | | | | | | -> Exit |
|---|---|---|---|---|---|---|---|---|---|
| Screw structure | DF | DF | DF | CF | DF | DF | DF | BL | DF |
| Sleeve lengths (mm) | 100 | 100 | 75 | 25 | 75 | 100 | 50 | 50 | 25 |
| Screw pitch lengths (mm) | 33 | 25 | 16.6 | -16.6 | 16.6 | 25 | 16.6 | — | 16.6 |

Figure 1:
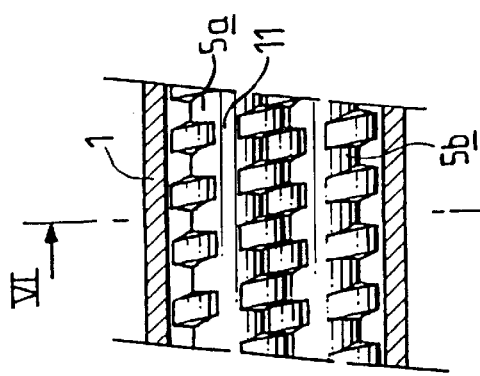
FIGS. 1, 3 and 5 show in elevation sections of different types of sleeves employed on the mixer shafts used in Example 1.

With reference to the drawing, it can be seen that 1 has been used to denote the outer casing of the mixer and 2a, 2b the axles of the two parallel shafts which are arranged therein. Adjacent sleeves are fitted onto the axles 2a, 2b, the two shafts being equipped with the same sleeves over the same section of the length to interact mechanically with each other during the rotation.

Figure 2:
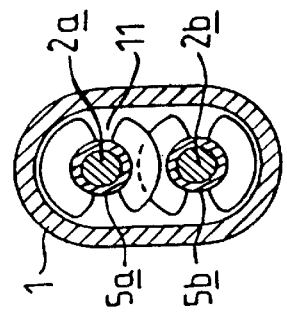
FIGS. 2, 4 and 6 show, respectively, cross-sections along II—II, IV—IV and VI—VI of FIGS. 1, 3 and 5.
Figure 3:
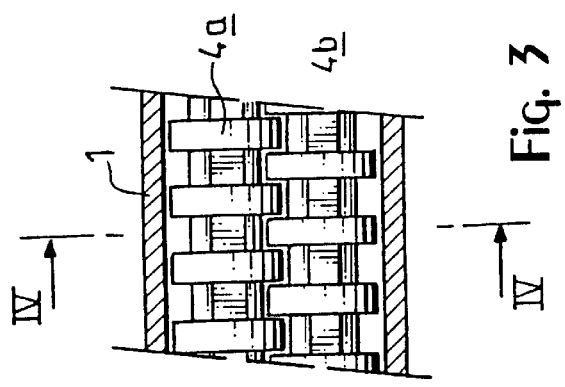
Figure 4:
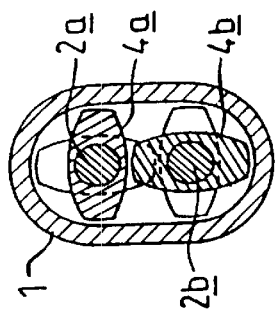
Figure 5:
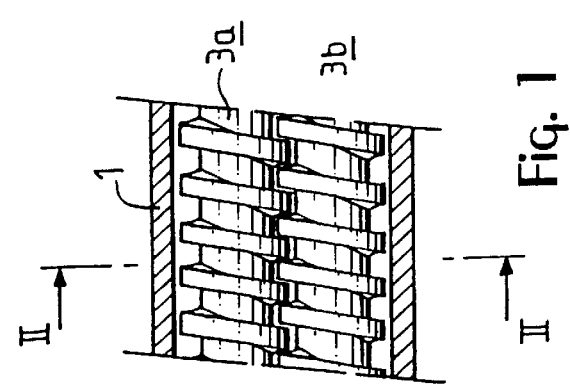
Figure 6:
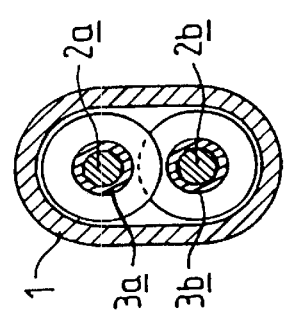

FIGS. 1 and 2 show a section where sleeves of "DF" type, given references 3a, 3b, are situated. FIGS. 3 and 4 show a section where sleeves 4a, 4b of the "BL" bilobar type are situated. A section where sleeves 5a, 5b of "CF" type with lengthwise grooves 11 are situated is shown in FIGS. 5 and 6.

In the table given above:

DF denotes a screw component with double helical flight, as illustrated in FIGS. 1 and 2;

BL denotes a bilobar component, as illustrated in FIGS. 3 and 4; and

CF denotes a screw component with DF reverse pitch, as illustrated in FIGS. 5 and 6, comprising length-wise grooves 11.

The various components have an external diameter of 25 mm, an internal diameter of 14 mm; the distance between the axles of the two shafts is 21 mm.

The two shafts rotate at a rate of 300 rev/min; the exit orifices have a total section of 500 $mm^2$; the throughput is approximately 5 kg/h.

The mixer described above has a length of 600 mm between the shaft head and the extrusion die. Its outer casing is arranged inside six adjacent muffs (not shown in the drawing) where thermostated fluids circulate, each muff occupying a length of 100 mm. The liquid circulating in the two muffs close to the shaft head is at 80° C., that circulating in the two muffs close to the extrusion die is at 20° C. and that circulating in the two intermediate muffs is at 60° C. In the case of the examples which follow, the pulverulent fraction is introduced with the aid of a weight-metering device at the shaft head and, optionally, partly at 100 mm from the extrusion die. The fatty phase is introduced with the aid of a peristaltic pump at the shaft head. The aqueous phase is introduced with the aid of a peristaltic pump at 100 mm from the shaft head. However, if the emulsion phases contain heats sensitive constituents such as a volatile silicone or certain stabilizers, these constituents may be introduced at 100 mm from the extrusion die. It is within the competence of a person skilled in the art, in the case of each specific composition, to control the temperature and to define the points of introduction to obtain the optimum cosmetic quality of the composition according to the invention.

B—Formulation

A powdered foundation blurring the relief of the skin is produced.

The formulation is the following (weights given in grams):

| | |
|---|---|
| Yellow iron oxide | 1.04 |
| Red-yellow iron oxide | 0.52 |
| Black iron oxide | 0.14 |
| Titanium dioxide | 6.3 |
| Triethanolamine | 0.69 |
| Stearic acid | 1.38 |
| Glyceryl stearate | 1.38 |
| Stabilizer | 0.1 |
| Isoparaffin | 4.41 |
| Expanded microspheres sold by the "Kemanord Plast" company under the trade name "Expancel" | 0.59 |
| Silica microspheres sold by the "Miyoshi" company under the trade name "Silicabeads SB 700" | 44.41 |
| Talc | 5 |
| Water q.s. | 100 |

In the case of this formulation the relative density D of the pulverulent fraction is 0.4656(the corresponding value of F0 is 31.9%); the filler content F is 50%; the value of C is approximately 90% and the value of C* is 33.75%.

A powdered foundation is obtained which can be applied to the face by means of a latex sponge; a uniform application of approximately 1 gram over the whole face produces a make-up blurring the relief of the skin but preserving a natural appearance.

EXAMPLE 2: PREPARATION OF A COMPACTED FOUNDATION

The operation is carried out in the same cooker-extruder mixer as in Example 1 with the same screw structure, the same temperatures, the same shaft speeds and the same exit orifices.

The formulation of the composition is the following (weights given in grams):

| | |
|---|---|
| Yellow iron oxide | 0.55 |
| Red-yellow iron oxide | 0.55 |

-continued

| | |
|---|---|
| Black iron oxide | 0.25 |
| Titanium dioxide | 3.65 |
| Triethanolamine | 1.1 |
| Stearic acid | 2.2 |
| Glyceryl stearate | 2.2 |
| Stabilizer | 0.3 |
| Isoparaffin | 5 |
| Expanded microspheres sold by the "Kemanord Plast" company under the trade name "Expancel" | 2 |
| Silica microspheres sold by the "Miyoshi" company under the trade name "Silicabeads SB 150" | 30 |
| Polymethyl methacrylate microspheres sold by the "Seppic" company under the trade name "Micropearl" | 8 |
| Water | 42.20 |

In the case of this formulation the relative density D of the pulverulent fraction is 0.6465 (which corresponds to a value F0=40%); the filler content F is 45%; the value of C is approximately 85% and the value of C* is 46.9%.

The extruded product obtained is formed by compacting in a mechanical press and then left in the open air. The compacted make-up product does not show any sign of cracking with time. When applied to a face at a rate of 1 gram per face, this powder has a very good hiding power and gives a make-up of natural appearance.

EXAMPLE 3: COMPACTED POWDER FOUNDATION

The operation is carried out in the same mixer as in Example 1 with the same operating conditions of the mixer.

The formulation of the composition is the following (weight given in grams):

| | |
|---|---|
| Yellow iron oxide | 0.55 |
| Red-yellow iron oxide | 0.55 |
| Black iron oxide | 0.25 |
| Titanium dioxide | 3.65 |
| Triethanolamine | 1.1 |
| Stearic acid | 2.2 |
| Glyceryl stearate | 2.2 |
| Stabilizer | 0.3 |
| Isoparaffin | 5 |
| Talc | 20 |
| Silica microspheres sold by the "Miyoshi" company under the trade name "Silica Bead SB 150" | 30 |
| Glycerine | 5 |
| Water | 29.20 |

In the case of this composition the relative density D of the pulverulent fraction is 2.44 (which corresponds to a value F0=40%); the filler content F is 50% ; the value of C is approximately 85% and the value of C* is 34.40%.

The extruded product obtained is compacted in a mechanical press and then left in the open air; no crack is found in the course of time. This product forms a foundation which can be applied to the face; at a rate of 1 gram per face it is found that the foundation has a very good hiding power and that it makes it possible to obtain a homogeneous make-up of natural appearance.

EXAMPLE 4: MAKE-UP GEL

A make-up gel is produced by employing the foundation obtained in Example 1; this foundation is converted into granules at the exit of the extruder mixer by virtue of a granulator fitted directly onto the extruder. The granules are incorporated into a gel consisting of 95% of water and 5% of carboxymethyl cellulose. 20% by weight of granules are incorporated into this gel; the granules have a mean size of approximately 1 mm.

When this gel is employed for making up a face it is found that the application gives a sensation of coolness and, after drying, a fine film of powder remains, which gives a very natural coloring and blurs the wrinkles.

EXAMPLE 5

The foundation of Example 1 is employed for forming a make-up rod (or stick) by molding. The make-up stick is stored under leakproof packaging; it makes possible a foundation application which gives a very good blurring of the reliefs of the skin.

What is claimed is:

1. An extruded homogeneous, cosmetic composition for making up the skin including a pulverulent fraction of particles comprising a filler and, optionally, a pigment; dispersed in a binder consisting of an emulsion of a fatty phase and an aqueous phase; said pulverulent fraction, fatty phase and aqueous phase having been mixed prior to extrusion, by simultaneously introducing said fatty phase, aqueous phase and pulverulent fraction into a cooker-extruder mixer, wherein said cooker-extruder mixer comprises:

(a) an entry end, (b) and exit end, (c) an outer casing provided with an extrusion die at the exit end, and (d) a shaft driven in rotation within the outer casing so that a peripheral structure of the shaft interacts with the outer casing and if there is a second shaft with a peripheral structure of the second shaft, to ensure blending of said constituents and movement of said cosmetic composition in the outer casing toward the extrusion die, wherein:

said pulverulent fraction comprises particles and, optionally, a pigment;

and said particles having a relative density D and a dimension of between 0.5 and 100 $\mu$m; said particles being present in a concentration per unit volume of at least a critical particle concentration C* which is the concentration by volume of the particles relative to the nonvolatile fraction of the binder at which the amount of nonvolatile fraction of the binder fills the interstices between said particles; and said filler being present at a concentration F, defined by the formula:

$$F = 100 \times \frac{\left(\begin{array}{c}\text{weight of the pulverulent} \\ \text{fraction excluding pigment}\end{array}\right)}{\text{(total weight of the composition)}}$$

which is between F0 and 1.8×F0, wherein F0 is calculated as follows:

F0=10 if D$\leq$0.1,

F0 =(60×D)+4 if 0.1<D$\leq$0.6, and

F0=40 if D>0.6.

2. The composition of claim 1, wherein C is greater than 80%; C being defined by the formula $$C = \frac{V_{CT}}{V_{CT} + V_G},$$

wherein $V_{CT}$ is the volume of the pulverulent fraction, and $V_G$ is the volume of the nonvolatile constituents of the fatty phase of the binder.

3. The composition of claim 1, wherein if D is greater than 0.6, then F is between 40% and 65%.

4. The composition of claim 1 wherein the pulverulent fraction contains a pigment.

5. The composition of claim 1, wherein the pulverulent fraction includes at least one noncompactable filler.

6. The composition of claim 4 wherein said pigment is at least one pigment selected from the group consisting of inorganic pigments, organic pigments, white pearlescent pigments and colored pearlescent pigments.

7. The composition of claim 1, wherein said filler is selected from the group consisting of starch, zinc oxide, titanium oxide, precipitated calcium carbonate, metal soaps derived from carboxylic organic acids containing 8 to 22 carbon atoms, silica and silicone powders.

8. The composition of claim 1 wherein said filler is a synthetic polymer powder.

9. The composition of claim 1 wherein said filler is an organic powder.

10. The composition of claim 1 wherein said filler is a fluorinated powder.

11. The composition of claim 1 wherein said filler is selected from the group consisting of a solid microsphere, an impregnated solid microporous microsphere and an unimpregnated solid microporous microsphere.

12. The composition of claim 1 wherein said filler is a polymeric microcapsule.

13. The composition of claim 1 wherein said filler is a hollow microsphere.

14. The composition of claim 1 containing from 25 to 50% by weight of water.

15. The composition of claim 1 containing from 30 to 45% by weight of water.

16. The composition of claim 1 wherein said fatty phase contains at least one constituent selected from the group consisting of a fatty oil of vegetable origin, a fatty oil of animal origin, a fatty oil of mineral origin, a fatty oil of synthetic origin, a wax of vegetable origin, a wax of animal origin, a wax of mineral origin and a wax of synthetic origin.

17. The composition of claim 1 wherein said fatty phase contains at least one of an oil-soluble ingredient and a lipophilic cosmetic agent, the combination of said ingredient and agent representing not more than 20% by weight relative to the total weight of the fatty phase.

18. The composition of claim 1 wherein said fatty phase contains volatile oils which at 25° C. have a saturated vapor pressure greater than 50 pascals, said volatile oils representing less than 10% by weight relative to the total weight of the composition and less than 20% by weight relative to the weight of the fatty phase.

19. The composition of claim 1 wherein said aqueous phase further comprises at least one additive selected from the group consisting of thickeners, moisturizers and hydrating agents, said additives representing not more than 40% by weight relative to the total weight of the composition.

20. The composition of claim 1 wherein said particles are selected from the group consisting of magnesium carbonate and magnesium hydrocarbonate.

21. The composition of claim 1, wherein C* is between 10 and 80%.

* * * * *